United States Patent
Collis et al.

(10) Patent No.: US 6,265,224 B1
(45) Date of Patent: *Jul. 24, 2001

(54) SAMPLE PROCESSING METHOD USING ION EXCHANGE RESIN

(75) Inventors: Matthew P. Collis, Seven Valleys, PA (US); Anne B. Brown, Ellicott City, MD (US); Oscar J. Llorin, Catonsville, MD (US); Thomas L. Fort, Finksburg, MD (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/328,575

(22) Filed: Jun. 9, 1999

Related U.S. Application Data (62) Division of application No. 08/963,934, filed on Nov. 4, 1997.

(51) Int. Cl.$^7$ ................................................. G01N 1/18
(52) U.S. Cl. .................... 436/178; 436/174; 436/176; 436/177; 435/91.2; 435/183; 435/184; 521/25; 536/24.5; 204/524; 204/632; 204/647; 210/638; 210/660; 210/661; 210/263; 205/792.5
(58) Field of Search .................... 435/91.2, 183, 435/184; 521/25; 536/24.5; 204/524, 632, 647; 205/792.5; 210/638, 660, 661, 263; 558/464; 568/605; 436/174, 176, 177, 178

(56) References Cited

U.S. PATENT DOCUMENTS

| | | | |
|---|---|---|---|
| 4,971,760 | * 11/1990 | Rubinstein | 422/37 |
| 5,654,141 | * 8/1997 | Mariani et al. | 435/6 |
| 5,660,984 | 8/1997 | Davis et al. | 435/6 |

FOREIGN PATENT DOCUMENTS

| | | |
|---|---|---|
| 0 269 764 A1 | 12/1986 | (EP) . |
| 0 270 017 A2 | 11/1987 | (EP) . |
| 0 747 387 A2 | 7/1990 | (EP) . |
| 0 626 456 A1 | 5/1994 | (EP) . |
| 0745849 A2 | * 4/1996 | (EP) . |
| 0 770 689 A2 | 9/1996 | (EP) . |
| WO 92/08807 | 5/1992 | (WO) . |
| WO 95/14087 | 5/1995 | (WO) . |
| WO 98/12351 | 3/1998 | (WO) . |

OTHER PUBLICATIONS

Erlich, Henry A., PCR Technology, pp33–34 (1989).
Ochert, A.S. et al., PCR Methods and Applications, 3:365–368 (1994).
Frickhofen, N. et al., J. Virol. Methods, 35:65–72 (1991).
Zeldis, Jerome B. et al., J. Clin. Invest., 84:1503–1508 (1989).
Grimprel, E. et al., J. Clin. Microbiol., 29:1711–1718 (1991).
Jiang, X. et al., J. Clin. Microbiol, 30:2529–2534 (1992).
Wilde, J. et al., J. Clin. Microbiol., 28:1300–1307 (1990).
Khan, G. et al., J. Clin. Pathol., 44:360–365 (1991).
Buffone, G.J., Clin. Chem., 37:1945–1949 (1991).
Hattori et al. J. Gen. Appl. Microbiol. 18, 271–283 (1972).*
Walsh et al. BioTechniques. 10(4): 506–513. 1991.*
Mariani et al. Molecular Biotechnology. 4:227–237. 1995.*
Altschmied et al. BioTechniques. 23(2): 228–229. Aug. 1997.*
Walters et al. Industrial and Engineering Chemistry. 47(1): 61–67. 1955.*
SIGMA Product Information Sheet. Amberlite MB–150. Sep. 6, 1996.*

* cited by examiner

*Primary Examiner*—W. Gary Jones
*Assistant Examiner*—Juliet C. Einsmann
(74) *Attorney, Agent, or Firm*—David W. Highet (57) ABSTRACT

The present invention relates to methods in which ion exchange resins are used to reduce the amount of substances which interfere with nucleic acid hybridization in samples. The methods also stabilize the samples. Kits containing the ion exchange resins render the methods convenient to use.

4 Claims, 2 Drawing Sheets

SAMPLE PROCESSING METHOD USING ION EXCHANGE RESIN

This is a division of U.S. patent application Ser. No. 08/963,934, filed Nov. 4, 1997.

BACKGROUND OF THE INVENTION

The field of the present invention broadly relates to nucleic acid hybridization and/or amplification. More specifically, the present invention relates to the reduction of substances in samples which interfere with nucleic acid hybridization and/or enzymatic amplification events. Such events include nucleic acid probe hybridization to determine the presence and/or amount of a target nucleic acid, nucleic acid primer hybridization for nucleic acid amplification processes and enzymatic activity including nucleic acid extension, nicking and/or cleavage. The present invention also relates to the removal of fluorescent compounds from samples, which increases sensitivity of fluorescent detection assays. Additionally, the invention relates to the stabilization of such samples which permits increased room temperature storage times. The present invention also relates to concentration of organisms.

Nucleic acid amplification processes such as strand displacement amplification (SDA), polymerase chain reaction (PCR), ligase chain reaction (LCR), nucleic acid sequence based amplification (NASBA), transcription mediated amplification (TMA) and others are used to create multiple copies of a particular nucleic acid sequence(s) of interest (target sequence) which is present in lesser copy number in a sample. However, a number of substances commonly found in such samples interfere with nucleic acid amplification processes. Similarly, such substances may interfere with or inhibit direct nucleic acid probe hybridization reactions used for the detection of target nucleic acids.

An example of a nucleic acid amplification inhibitory substance is porphyrin compounds derived from heme and hematin which are both commonly found in blood samples and inhibit PCR. (*PCR Technology*, Stockton Press, Henry A. Erlich, Ed. pp 33–34, 1989). Protocols using osmotic lysis and pelleting of nucleic and cell debris have been used to reduce the amount of these inhibitors.

Salivary samples have also been reported to contain PCR inhibitory substances. Ochert et al., *PCR Methods and Applications* 3, 365–368 (1994). Although the inhibitory substances were not identified, it was found that extended microwaving or boiling of the salivary sample totally removed PCR inhibition.

Frickhofen and Young, *J. Virol. Methods* 35, 65–72 (1991), report that heating of serum samples for 45 seconds at 70° C. improves PCR amplification of viral nucleic acid sequences. This improvement is theorized to be due to heat inactivation of serum enzymes such as aprotinin, leupeptin PMSF and pepstatin which are believed to be inhibitory to PCR processes.

Another approach for removing PCR inhibitory substances from serum prior to amplification of a viral nucleic acid sequence is taught by Zeldis et al., *J. Clin. Invest.* 84, 1503–1508 (1989). This approach involves adsorbing the virus to antibody coated microparticles, washing the microparticles, and then destroying the remaining proteins which may be inhibitory to PCR with proteinase K.

In attempting to detect *Treponema pallidum* in amniotic fluid, fetal and neonatal sera and cerebrospinal fluid by PCR, four different processes were attempted to remove PCR inhibitory compounds. Grimprel et al., *J. Clin. Microbiol.* 29, 1711–1718 (1991). Briefly, the four processes for removal of PCR inhibitory compounds were: (1) a boiling method wherein sample in a tube was placed in a boiling water bath for 10 minutes, cooled on ice, and then centrifuged; (2) a low-spin separation method wherein sample was added to sterile phosphate buffered saline and subjected to a series of centrifugations, then the pellet was resuspended and boiled for 10 minutes, after which it was cooled on ice; (3) an alkaline lysis extraction method wherein sample was boiled for 1.5 minutes in 1 M NaCl, 1 N NaOH and 0.1% SDS, then neutralized with 0.5 M Tris-HCl (pH 8.0), and then subjected to a series of extractions with phenol and chloroform-isoamyl alcohol, and precipitated with isopropyl alcohol; and (4) a spin extraction method wherein sample was subjected to low-spin separation as described in (2) above, followed by 10 minutes of boiling and one phenol-chloroform extraction before precipitation in cold absolute ethanol. The authors reported varying success of these methods dependent on the type of samples used.

With stool samples, polyethylene glycol precipitation was found to remove a significant amount of small particles and soluble substances which could be inhibitory to a reverse transcriptase-PCR process. Jiang et al., *J. Clin. Microbiol.* 30, 2529–2534 (1992). Following the precipitation, an extraction process was performed using the cationic detergent, cetyltrimethylammonium bromide (CTAB) in a high salt concentration in conjunction with phenol-chloroform extraction.

A different approach to removal of PCR inhibitory substances from stool samples is reported by Wilde et al., *J. Clin. Microbiol.* 28, 1300–1307 (1990). Before using PCR to detect rotavirus nucleic acid from stool samples, the extraction process was modified with an added step that utilized chromatographic cellulose fiber powder (CF11 powder) to purify the rotavirus RNA during a series of rapid washing and elution steps.

When performing a study to detect cytomegalovirus (CMV) in urine using PCR, it was found that urea is inhibitory to PCR. Khan et al., *J. Clin. Pathol.* 44, 360–365 (1991). This reference reports that the PCR inhibitory effects of urea in urine are effectively removed by simple dialysis or ultracentrifugation.

Another process to remove PCR inhibitory substances from urine before detection of CMV nucleic acid is reported by Buffone et al., *Clin. Chem.* 37, 1945–1949 (1991). This process occurs subsequent to release of the nucleic acid from the CMV organisms and uses fine glass beads to adsorb nucleic acid such that protein and other substances can be selectively eluted before recovery of the nucleic acid for amplification.

As evidenced by the references described above, most of the publication regarding nucleic acid amplification inhibition has related to PCR. However, these same substances which are inhibitory to PCR, as well as a number of other substances commonly found in clinical samples such as proteinaceous substances, EDTA, human DNA and iron have been found to be inhibitory to SDA, and other nucleic acid amplification processes as well.

Also, most of these methods to reduce or remove inhibiting substances involve rather time-consuming complicated steps which must be added to the sample processing methodology. Another problem with methods which utilize relatively severe processing steps or conditions, and/or require separation of target nucleic acid from other substances is the loss of some target nucleic acid sequence. Despite the ability of nucleic acid amplification processes to make multiple copies of target sequence (amplicons) from very few original targets, amplification efficiency and detection ability are improved if there are greater numbers of original targets in the sample. The greater detection ability can be very important when processing particularly difficult to detect samples such as acid fast Bacillus (AFB) smear negative *Mycobacterium tuberculosis* samples.

Another common problem with samples to be subjected to a molecular diagnostic process is the stability of the sample over time. Stability of the sample becomes more important when samples are taken at one location, but are then transported to another location such as a centralized laboratory for molecular diagnostic processing.

Many clinically relevant organisms do not maintain their integrity in urine samples and vaginal and cervical swabs for more than about twenty-four (24) hours at room temperature. Thus, refrigeration of such samples during transport to centralized laboratories and/or during storage has become a necessity. One analyte which is commonly tested from urine samples and swabs and is notoriously unstable in samples stored at room temperature is *Neisseria gonorrhoeae*.

SUMMARY OF THE INVENTION

In order to address the problems associated with the presence of substances inhibitory to nucleic acid hybridization and/or amplification and thus, achieve the benefits of improved detection of target nucleic acid sequences, the present invention provides a method for reducing the amount of such substances in samples by exposing the sample to an ion exchange resin prior to lysis of cells in the sample.

All classes of ion exchange resins (cation, anion and mixed bed) are potentially useful in the present invention. Also, following exposure of the sample to the ion exchange resin, the ion exchange resin may be separated from the sample.

By using the ion exchange resins in dried form, an added benefit is the concentration of target organism. The exposure of sample to ion exchange resin also stabilizes the sample for storage or transport at room temperature, and permits the binding and removal of fluorescent substances from a sample which may interfere with subsequent fluorescence based detection assays. Furthermore, the ion exchange resin can be packaged in kit form for ease of use.

BRIEF DESCRIPTION OF THE DRAWINGS

The various objects, advantages and novel features of the present invention will be readily understood from the following detailed description when read in conjunction with the appended drawings in which.

DETAILED DESCRIPTION OF THE INVENTION

As stated above, the present invention relates to a method for reducing the amount of substances which interfere with, or are inhibitory to, nucleic acid hybridization and/or amplification processes from samples containing cells with nucleic acid. In the method, the sample is exposed to an ion exchange resin prior to lysis of cells in the sample such that cells containing nucleic acid will remain in the sample. Then, optionally, such cells may be separated from the ion exchange resin.

The results of this method were particularly unexpected because of the complexity of some of the processes tried by others to remove inhibitory substances as evidenced by the descriptions in the Background section above. Also, to the inventort's knowledge, ion exchange resins are not typically utilized prior to lysis of samples which are to be subjected to nucleic acid hybridization and/or amplification reactions.

Also, one of the advantages of the method of the present invention is the ability to increase the final concentration of target nucleic acid from the cells in a sample. Although nucleic acid amplification processes are capable of creating many copies of a target sequence (amplicons) from very few initial targets, it is beneficial to start the amplification process with as many initial targets as possible. Concentration occurs as a result of the swelling of the dry matrix. Liquid from the sample is taken up or absorbed by the dry resin while the cells are too large to enter the resin. The resultant decrease in available sample liquid coupled with the constant number of cells, yields an increase in cell concentration. In the case of AMBERLITE™ MB-150, the dry resin absorbs up to 50% of its dry weight. Other processes for removing nucleic acid hybridization inhibitory substances subsequent to lysis of the cells are notoriously inefficient, because they are based on separation of nucleic acid from other substances in the lysate, and thus, many initial targets are not recovered. In the present method, where the inhibitory substances are removed prior to cell lysis, such subsequent separation is not necessary, and better yields of initial target are achieved.

The samples which may be subjected to the method of the present invention include virtually all human and veterinary clinical samples such as sputum samples, blood samples, urine samples, cerebrospinal fluid ("CSF") samples, vaginal and cervical swabs and others, environmental samples such as water, air and soil samples, and food samples. The samples which may be subjected to the method of the present invention are suspected of containing cells with a target nucleic acid sequence to be subjected to a hybridization process such as direct probe hybridization or primer hybridization for initiation of an amplification process.

Substances which are inhibitory to nucleic acid hybridization processes and typically found in such samples include proteinaceous materials, non-target DNA, salts, urea, and proteolytic enzymes. As discussed in the Background section above, these substances are known to be inhibitory of nucleic acid amplification processes such as SDA, PCR, LCR, NASBA, TMA and others.

The method of the present invention involves the exposure of the sample to an ion exchange resin. This exposure may occur at any time prior to the lysis of cells to release target nucleic acid.

Many ion exchange resins are useful in the method of the present invention. Examples of such useful ion exchange resins include resins such as those referred to as AMBERLITE™ resins available from Sigma-Aldrich, and similar resins. Typically, these ion exchange resins are in the form of a polymer such as polystyrene with charged functional groups attached thereto or incorporated therein. Thus, the polymer may bind inhibitors such as proteins and enzymes hydrophobically and the charged functional groups bind charged inhibitors such as salts, extracellular nucleic acids and protein. Other resins useful in the method of the present invention can be identified by one of ordinary skill in the art with a reasonable expectation of success by performing routine screening assays directed towards the optimal characteristics of such resins, e.g., removal of inhibitory substances and maintenance of the integrity and/or viability of the target organisms after exposure to the resin.

Briefly, a sample containing target organisms is treated with an ion exchange resin for a period of time. The sample is subjected to the hybridization/amplification test of interest. A marked increase in hybridization and/or amplification efficiency following exposure to the resin would indicate efficacy of the resin.

Alternatively, or additionally, a sample is exposed to an ion exchange resin, beyond the amount of time which a particular sample is known to be stable at room temperature. For example, a N. gonorrhoeae urine sample is generally stable for no more than about twenty-four hours at room temperature. Thus, after such exposure, the sample is plated to determine whether the particular analyte, (i.e. N. gonorrhoeae) is still viable. Those ion exchange resins which allow the maintenance of the analyte's integrity and/or viability at room temperature beyond the no-resin control would be useful in the method of the present invention.

The concentration and amount of the ion exchange resin used in the method of the present invention is dependent on the type of sample being subjected to the method. Generally, the amount of the ion exchange resin used in the method of the present invention is in a mass to mass ratio with the sample within the range of about 1:1 to about 1:20, with a preferred range of about 1:5 to about 1:15. With most samples, a ratio of approximately 1:10 is appropriate. By using the screening method described for selection of a suitable resin, one skilled in the art could vary the ratio of resin to sample volume to achieve results similar to the present invention.

The resin may be presented to the sample in a variety of forms. Examples of suitable forms of the resin for use in the methods of the present invention include a dry granular form, a compressed tablet of resin, a dissolvable capsule containing resin, a permeable vehicle such as a sack containing the resin and ion exchange paper such as Ion Exchange Cellulose Papers Grade P 81 available from Whatman and S&S Ion-Exchange Membranes available from Schleicher & Schuell. Any of these forms may be packaged by itself or with other components in a kit for: (a) the removal from a sample of substances which interfere with nucleic acid hybridization and/or amplification; (b) the stabilization of a sample in order to permit increased room temperature storage time; (c) the removal of fluorescent compounds from a sample in order to increase the sensitivity of fluorescent detection assays; and/or (d) the concentration of organisms in a sample.

A permeable vehicle containing resin is a preferred means for permitting contact of resin and sample. Such a permeable vehicle acts much like a tea bag permitting a liquid sample to flow over the resin, but also permitting easy separation of the resin from the sample without the need for an additional centrifugation or filtering step. Generally, the permeable vehicle is a mesh containing the ion exchange resin.

Figure 1:
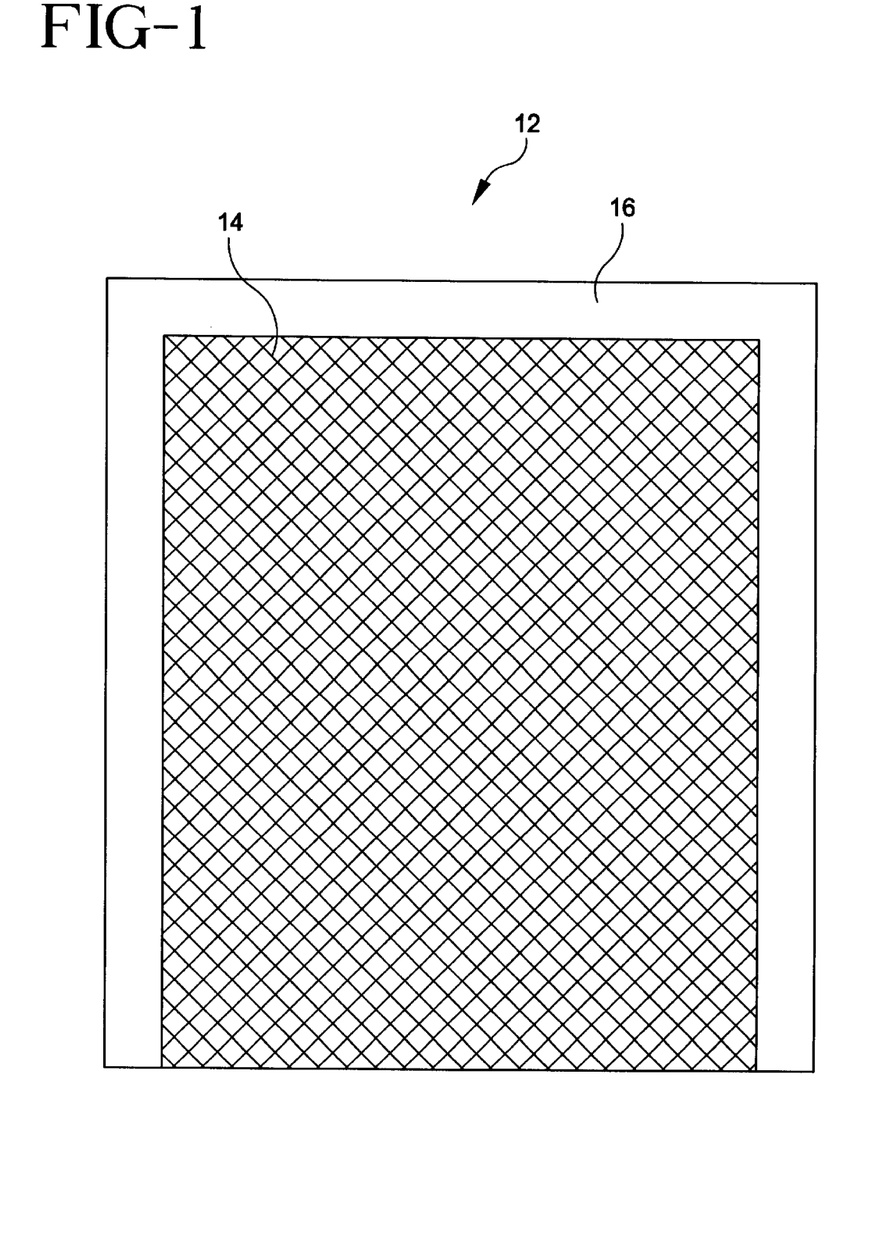
FIG. 1 shows an front view of a kit or vehicle for exposure of an ion exchange resin to a sample.
Figure 2:
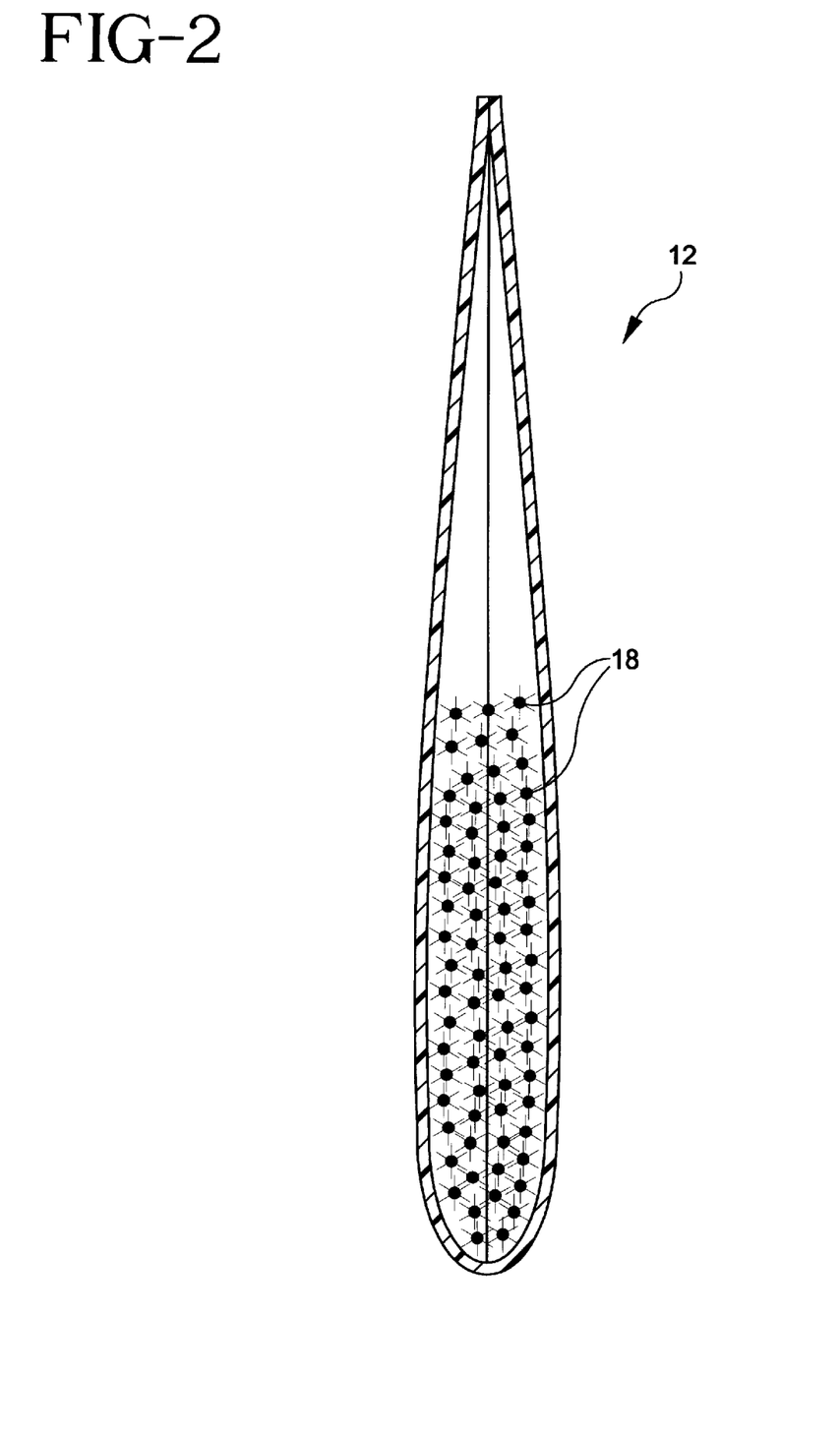
FIG. 2 shows a cut-away side view of the kit or vehicle of FIG. 1.

One embodiment of such a permeable vehicle is shown in FIGS. 1 and 2. FIG. 1 is a front view of the vehicle (12) which is constructed of a unitary sheet of mesh (14) with a border (16) which is either created upon heat sealing of the mesh, or may be constructed of an adhesive or sealable material other than the mesh. As shown in FIG. 1, the unitary sheet is folded back upon itself to create the vehicle (12).

During construction, the two sides of the unitary sheet are sealed after the sheet is folded back upon itself. Then, an appropriate amount of the ion exchange resin (18) (see FIG. 2) is added from the open top of the vehicle. Following addition of the ion exchange resin, the top of the vehicle is crimped and sealed as well. This creates the vehicle shown in cut-away side view in FIG. 2.

Suitable materials for the mesh (14) such vehicles include, but are not limited to, polypropylene and nylon. The same materials are also suitable for the adhesive or sealable border (16).

When the resin is contacted with the sample, nucleic acid hybridization and/or amplification inhibitory substances adhere to the resin. The principal means by which the ion exchange resin binds inhibitory substances is by exchange of cations and anions of the resin for the inhibitory substances. Thus, innocuous cations and anions are released into the sample, and the inhibitory substances are bound to the resin. Then, such substances are removed from the sample prior to the commencement of any nucleic acid hybridization and/or amplification event.

The amount of time for contact of the resins and sample is dependent upon the type of sample, the ratio of resin to sample, and the concentration and type of inhibitors in the sample. Although the resin is active immediately upon contact with the sample, the time of contact of resin and sample for the method of the present invention is about fifteen (15) minutes to about four (4) days.

Optionally, following such contact, the resin and sample may be separated. As stated above, such separation may be conducted by a variety of means such as centrifugation, filtering, or if the permeable vehicle or ion exchange paper are used, then the matrix (permeable vehicle or ion exchange paper) can be physically removed from the sample or the treated sample can simply be removed by pipetting.

A variety of processes are currently used to prepare target nucleic acids in samples for hybridization or amplification. For example, sputum samples which are processed to amplify mycobacterial nucleic acid sequences are typically subjected to a NALC/NaOH process. Similarly, other types of clinical samples are subjected to other well known standard processes, for example, centrifugation for large volume samples such as blood and urine. The method of the present invention may be used before, as part of, or after those standard processes.

In addition to utility in the method for removing nucleic acid hybridization and/or amplification inhibitory substances, the contacting of ion exchange resin with sample also stabilizes such sample for transport at room temperature and concentrates the sample. The amount of resin useful for such transport stabilization is about the same as for removing nucleic acid hybridization and/or amplification inhibitory substances. Transport stabilization, sample concentration, removal of fluorescent substances, and removal of nucleic acid inhibitory substances all occur as a result of contacting an ion exchange resin with the sample. Thus, the present invention provides an extremely efficient method for one to stabilize a sample at room temperature for transport or other reasons, and simultaneously commence the processing or preparation of such sample for a molecular diagnostic assay by concentrating the sample and binding fluorescent compounds and nucleic acid hybridization and/or amplification inhibitory substances for subsequent removal from the sample.

The following examples illustrate specific embodiments of the invention described herein. As would be apparent to skilled artisans, various changes and modifications are possible and are contemplated within the scope of the invention described.

EXAMPLE 1

A Mixed Bed Ion Exchange Resin Removes a Known Amplification Inhibitor and Background Fluorescent Compounds from Urine and Swab Samples The purpose of this Example was to determine if a mixed bed ion exchange resin (AMBERLITE™ MB-150) removes non-specific DNA from a urine sample and swab sample. In addition, fluorescent readings were taken of the treated and untreated samples to determine if fluorescent compounds, which would increase the background of a fluorescent detection system and potentially decrease the sensitivity of the system would be removed.

Materials
Sample Processing Reagents:
Vaginal swab samples collected with B-D E-Z swabs
Urine samples
Sample buffer
AMBERLITE™ MB-150 (Sigma)
BD polypropylene dispense tubes
ssDNA Assay Reagents:
Oligreen dye (Molecular Probes)
TE buffer
Procedure Eight vaginal swab samples were expressed into four ml of sample buffer, the solution was vortexed and one ml of the sample was dispensed into two BD dispense tubes containing AMBERLITE™ MB-150 at 0.4 gms. The solution in the BD dispense tubes was vortexed and was maintained at room temperature for 30 minutes. After 30 minutes the fluid was transferred to a separate tube.

One ml of urine was dispensed into two BD dispense tubes containing 0.4 gms of AMBERLITE™ MB-150. The solution was vortexed and was maintained at room temperature for 30 minutes. After 30 minutes the solution was vortexed and was then transferred to a separate tube.

Human placental DNA standards were prepared in TE buffer at 1000 ng/ml, 500 ng/ml, 250 ng/ml, 125 ng/ml, 62.5 ng/ml, 31.25 ng/ml and 0 ng/ml. Both AMBERLITE™ MB-150 treated samples and untreated urine and swab samples from above, were diluted 1:10 and 1:100 in TE buffer. The samples were placed in a boiling water bath for five minutes to denature the DNA strands. Oligreen dye was diluted 1:200 in TE according to the manufacturer's instructions. An equal volume of sample and diluted Oligreen dye was combined in plastic cuvettes and the samples were read using a fluorescent excitation wavelength of 480 and an emission wavelength of 520. Background fluorescent readings on the untreated samples were measured using the 480 excitation and 520 emission wavelengths and the background was subtracted from the ssDNA measurements. Background fluorescent readings were taken on the treated samples as well for comparison to the untreated samples, to determine if background fluorescence substances were removed.

Results

The results are provided in the table below, using those ssDNA values which fell on the linear portion of the standard curve.

| TREATMENT | SAMPLE | SSDNA CONC. (NG/ML) | % REDUCTION ssDNA | 520/480 READING | % REDUCTION FLUORESCENCE |
|---|---|---|---|---|---|
| NONE | SWAB | 31493 | — | 656 | — |
| AMBERLITE | SWAB | 14066 | 55.3 | 320 | 51.2 |
| NONE | URINE | 1417 | — | 8514 | — |
| AMBERLITE | URINE | 546 | 61.5 | 798 | 93.8 |

Conclusions

The data of this Example indicates that a mixed bed ion exchange resin removes background fluorescent compounds from both swab samples and urine samples. This result is beneficial as high background fluorescence can impact sensitivity claims in a fluorescent assay detection system. In addition, these data indicate that a mixed bed ion exchange resin removes non target DNA, a known amplification inhibitor of Strand Displacement Amplification (SDA).

EXAMPLE 2

Direct Method for Urine Processing

The purpose of this Example was to determine if the present invention could be used to eliminate the traditional centrifugation and wash steps in urine processing.

Materials
Sample Processing Reagents:
AMBERLITE™ MB-150 (Sigma)
Antifoam
Spectra/mesh® polypropylene filter, 75 um
Urine samples
2x chlamydia sample buffer
1x sample processing buffer
Chlamydia preparation
Assay Reagents:
Oligonucleotide Devices (ODs)—microtiter plates with SDA amplification primers, SDA bumper primers, SDA fluorescence detector probes, dUTP and buffers dried in each well
Enzyme Devices (ENDs)—microtiter plates with restriction endonuclease (BsoB1), polymerase (Bst), dCsTP, dATP, dGTP and buffers dried in each well (ODs and ENDs are more completely described in co-pending U.S. patent application Ser. No. 08/964,020 filed Nov. 4, 1997 the disclosure of which is specifically incorporated herein by reference).
Procedure Four urine samples were spiked at 1000 Chlamydia elementary bodies/ml. AMBERLITE™ MB-150 at 0.3 gms was dispensed into four BD dispense tubes containing ten ul of 1.25% anti-foam. One ml of each urine sample was added to one BD dispense tube containing AMBERLITE™ MB-150 and the samples were maintained at room temperature for 30 minutes. The solution was squeezed through a 75 um polypropylene mesh into a tube. An equal volume of sample and 2× concentrated sample buffer were dispensed into an tube/sample and the tubes were placed in a 105° C. heat block for 30 minutes.

Four ml of the urine sample was dispensed into tubes and the tubes were centrifuged at 2,000 g for 30 minutes. The supernatant was decanted and three ml of Sample buffer was added to the tube. These tubes were placed in a 105° C. heat block for 30 minutes.

Aliquots (~150 ul) of a sample from the tubes were dispensed into each well of the ODs. The wells of the ODs were covered, and the ODs retained at room temperature for 20 minutes. The ODs were then uncovered, and incubated at 75° C. for 10 minutes, while the ENDs were pre-warmed for 10 minutes to 52° C.

After the 10 minute incubation, 100 ul aliquots from each well of the ODs were transferred (pipetted) to a corresponding well in the ENDs. The ENDs were then sealed with an adhesive cover, and introduced into a fluorescence reader instrument as described in co-pending U.S. patent application Ser. No. 08/929,895, filed Sep. 15, 1997, the disclosure of which is specifically incorporated herein by reference. (Other standard microtiter plate fluorescence reader instruments could also be used.)

The fluorescence signal from the wells of the ENDs were monitored for 60 minutes. The sealed ENDs were then discarded in a sealed bag to further insure against potential amplicon contamination of the laboratory environment.

Results

The results are provided in the table below as units of area. Area is the integration of the fluorescent signal curve over time.

| Sample | AMBERLITE ™ Method (Area) | Control Method (Area) |
|---|---|---|
| F1 | 35774 | 29354 |
| M10 | 15622 | 8138 |
| M11 | 13127 | 2774 |
| M12 | 10322 | 14858 |

Conclusions

The data of this Example indicates that, centrifugation and associated wash steps can be eliminated from urine sample processing by incorporating the method of the present invention.

EXAMPLE 3

A Mixed Bed Ion Exchange Resin For Removal of Amplification Inhibition Using *Neisseria gonorrhoeae* Spiked Negative Clinical Samples The purpose of this Example was to determine if a mixed bed ion exchange resin (AMBERLITE™ MB-150) removes amplification inhibitors and improves the recovery of specific target signal compared to the control method.

Materials
Sample Processing Reagents:
Urine Samples
*Neisseria gonorrhoeae* preparation
Sample buffer
AMBERLITE™ MB-150 (Sigma)

Amplification Reagents:
ODs (as defined in Example 2, but containing SDA amplification primers, SDA bumper primers and SDA fluorescence detector probes specific for *N. gonorrhoeae* rather than Chlamydia)
ENDs
Procedure Thirty clinical urine samples were spiked with 1000 *Neisseria gonorrhoeae* particle forming units/ml. Six ml of each sample was transferred to a 15 ml conical tube containing 0.12 gms Amberlite MB-150. Each tube was vortexed and the tubes were stored at room temperature for sixteen hours. For the control conditions, four ml of each urine sample was transferred directly to a centrifuge tube and the samples were stored at 4° C. for sixteen hours.

After sixteen hours at room temperature the samples containing AMBERLITE™ were vortexed and four ml of fluid was transferred to centrifuge tubes. Both the urine samples treated with AMBERLITE™ and those samples stored at 4° C., without Amberlite MB-150, were centrifuged at 2,000 g for 30 minutes. The supernatant was decanted from each tube and three ml of sample diluent was added to each tube. The tubes were placed in a heat block at 105° C. for 30 minutes.

The samples were amplified and results detected using the same procedure as in Example 2.

Results

The results are provided in a table below using the mean area of three amplification/detection replicates. The values at the bottom of the table are the means for all the samples.

| Sample # | AMBERLITE ™ Treatment (area) | Control Method (area) |
|---|---|---|
| 1 | 6759 | 4441 |
| 2 | 24500 | 1766 |
| 3 | 17734 | 1157 |
| 4 | 9442 | 4836 |
| 5 | 1071 | 791 |
| 6 | 2419 | 1477 |
| 7 | 2252 | 1664 |
| 8 | 6704 | 2105 |
| 9 | 5013 | 1072 |
| 10 | 3934 | 1819 |
| 11 | 3711 | 1324 |
| 12 | 14138 | 1513 |
| 13 | 1059 | 532 |
| 14 | 1363 | 4258 |
| 15 | 9598 | 2203 |
| 16 | 8466 | 9474 |
| 17 | 16810 | 3295 |
| 18 | 11105 | 4312 |
| 19 | 4098 | 2420 |
| 20 | 13087 | 2341 |
| 21 | 2382 | 1080 |
| 22 | 7205 | 8649 |
| 23 | 675 | 3430 |
| 24 | 6626 | 1091 |
| 25 | 19012 | 3147 |
| 26 | 4980 | 790 |
| 27 | 7968 | 1324 |
| 28 | 11034 | 5179 |
| 29 | 22049 | 5904 |
| 30 | 8910 | 2462 |
| MEAN | 8470 | 2862 |

Conclusions

Mixed bed ion exchange resin treatment of urine samples produces statistically higher areas compared to control method of processing urine samples (based on T test results, using equal variance with a P value=2.36E-9), indicating that amplification inhibitors are removed from the system and specific amplification is performed more efficiently.

EXAMPLE 4

Comparative Example Showing Room Temperature Stability of Neisseria gonorrhoeae in Urine The purpose of this Example was to evaluate the stability of *Neisseria gonorrhoeae* in urine at room temperature.

Materials
Sample Processing Reagents:
Sample Diluent
*N. gonorrhoeae* stock
Urine—Male Urine Pool
Amplification Reagents:
ODs as in Example 3
ENDs as in Example 3

Procedure

*Neisseria gonorrhoeae* was spiked into a normal male urine pool to yield final reaction concentrations of 0, 10 and 100 particles per reaction. The dilutions were stored at 25° C. Four ml aliquots of each dilution were transferred to sample tubes for processing at the following time points: 0 hr, 1 day, 2 days and 4 days. All samples were processed as follows: Centrifuge 2000×g for 30 minutes, decant supernatant, resuspend pellet with 2 ml of sample diluent, heat 30 minutes at 100° C. The samples were amplified and results detected using the same procedure as in Example 2.

Results

Results are provided as mean areas in the table below.

| Storage Time | 0 pfu GC/rxn | 10 pfu GC/rxn | 100 pfu GC/rxn |
| --- | --- | --- | --- |
| 0 hours | 2376 | 5721 | 21506 |
| 1 day @ 25° C. | 3080 | 2415 | 12065 |
| 2 days @ 25° C. | 3355 | 4577 | 2797 |
| 4 days @ 25° C. | N/A | 2599 | 4483 |

Conclusions

*Neisseria gonorrhoeae* is unstable when stored in urine at room temperature for 1 day or longer.

EXAMPLE 5

Screening of Additives for Stability of Neisseria gonorrhoeae and Chlamydia trachomatis at Room Temperature The purpose of this Example was to screen additives for stability of *Neisseria gonorrhoeae* and *Chlamydia trachomatis* in urine at room temperature for two days.

Materials
Sample Processing Reagents:
Urine Pools
Sample buffer
ChemStat tube (MicroSure Inc.)
Boric Acid/Formate
ProClin 300
AMBERLITE™ MB-150 (Sigma)
Amplification Reagents:
*N. gonorrhoeae* ODs as in Example 3
*N. gonorrhoeae* ENDs as in Example 3
*C. trachomatis* ODs as in Example 2
*C. trachomatis* ENDs as in Example 2

Procedure

Three urine pools were spiked with 750 Elementary bodies/ml of Chlamydia strain LGV-II. Two of the three pools were spiked with 750 particles forming units/ml of *Neisseria gonorrhoeae*. The third pool was positive for *Neisseria gonorrhoeae* and was not spiked. Four ml of each urine pool was transferred to four tubes. At 0 hr, 40 hours at 4° C., 40 hours at 24° C. and 96 hr at 4° C. the tubes were centrifuged at 2,000 g for 30 minutes. The supernatant was decanted and three ml of sample buffer was added to each tube. The tubes were transferred to a heat block for 30 minutes at 105° C.

Ten ml of each pool was transferred to a ChemStat tube. The material was then transferred to two tubes/pool at four ml/tube. At 0 hr and 40 hours at 24° C. the tubes were centrifuged at 2,000 g for 30 minutes. The supernatant was decanted and three ml of sample buffer was added to each tube. The tubes were transferred to a heat block for 30 minutes at 105° C.

Five ml from each pool was transferred to two Boric Acid/Formate tubes/pool. The material from each Boric Acid/Formate tube was transferred to an tube at four ml. At 0 hr and 40 hours at 24° C. the tubes were centrifuged at 2,000 g for 30 minutes. The supernatant was decanted and three ml of sample buffer was added to each tube. The tubes were transferred to a heat block for 30 minutes at 105° C.

Nine ml from each pool was transferred to a 15 ml centrifuge tube containing 2.7 ul of ProClin 300. Four ml from each pool was transferred to two tubes. At 0 hr and 40 hours at 24° C. the tubes were centrifuged at 2,000 g for 30 minutes. The supernatant was decanted and three ml of sample buffer was added to each tube. The tubes were transferred to a heat block for 30 minutes at 105° C.

A 5.5 ml aliquot of each pool was transferred to two 15 ml centrifuge tubes containing 0.72 gms of AMBERLITE™ MB-150. Ten minutes after addition of the sample to Amberlite the solution was transferred to tubes at four ml. The remaining 15 ml centrifuge tubes containing each pool were stored at 40 hr at 24° C. The solution was transferred to tubes at four ml and the tubes were centrifuged at 2,000 g for 30 minutes. The supernatant was decanted and three ml of sample buffer was added to each tube. The tubes were transferred to a heat block for 30 minutes at 105° C.

The samples were amplified and the results detected using the same procedure as in Example 2.

Results

Results are indicated in the table below as the mean of three amplification replicates.

*Neisseria gonorrhoeae*

| | No addition | | | ChemStat | | Boric Acid/ Formate | |
| --- | --- | --- | --- | --- | --- | --- | --- |
| Sample | 0 hr 25° C. | 40 hr 4° C. | 40 hr 25° C. | 0 hr 25° C. | 40 hr 25° C. | 0 hr 25° C. | 40 hr 25° C. |
| Pool 1 | 19543 | 15970 | 5290 | 14003 | 2593 | 25843 | 5337 |
| Pool 2 | 21180 | 16682 | 403 | 7252 | 1854 | 12026 | 877 |
| Pool 3 | 27854 | 31367 | 30188 | 27486 | 21251 | 24511 | 24468 |

| | AMBERLITE ™ | | ProClin (0.03%) | |
| --- | --- | --- | --- | --- |
| Sample | 0 hr 25° C. | 40 hr, 25° C. | 0 hr 25° C. | 40 hr 25° C. |
| Pool 1 | 12094 | 27832 | 16925 | 4263 |
| Pool 2 | 22288 | 10288 | 14311 | 1117 |
| Pool 3 | 30564 | 28405 | 27790 | 30998 |

*Chlamydia trachomatis*

|  | No addition | | | ChemStat | | Boric Acid/ Formate | |
|---|---|---|---|---|---|---|---|
| Sample | 0 hr 25° C. | 40 hr 4° C. | 40 hr 25° C. | 0 hr 25° C. | 40 hr 25° C. | 0 hr 25° C. | 40 hr 25° C. |
| Pool 1 | 5235 | 11553 | 12145 | 18339 | 6625 | 49956 | 16963 |
| Pool 2 | 10708 | 3631 | 422 | 16139 | 432 | 19153 | 5781 |
| Pool 3 | 14490 | 804 | 19784 | 18110 | 5378 | 3734 | 4097 |

|  | AMBERLITE ™ | | ProClin (0.03%) | |
|---|---|---|---|---|
| Sample | 0 hr 25° C. | 40 hr, 25° C. | 0 hr 25° C. | 40 hr 25° C. |
| Pool 1 | 7145 | 22211 | 6378 | 21922 |
| Pool 2 | 43043 | 26650 | 22441 | 36003 |
| Pool 3 | 35559 | 34907 | 4097 | 19722 |

Conclusions

A mixed bed ion exchange resin (AMBERLITE™ MB-150) at 0.13 g/ml provides stability of *Neisseria gonorrhoeae* in urine for up to 40 hours at room temperature for Pools 1 and 2 which have known spike levels of *Neisseria gonorrhoeae*. Pool 3 which tested initially, very positive for *Neisseria gonorrhoeae* was positive for all storage conditions, which indicates that with very high concentrations of *Neisseria gonorrhoeae*, specific signal is maintained. ChemStat, Boric Acid Formate and ProClin additives provided little or no stability for *Neisseria gonorrhoeae* at room temperature.

AMBERLITE™ MB-150 was effective as both inhibitor removal and for stabilization of Chlamydia LGV-II.

EXAMPLE 6

Mixed Bed Ion Exchange Resin Treatment of Urine Stabilizes Individual Spiked Negative Clinical Samples for Four Days The purpose of this Example was to determine if *Neisseria gonorhhoeae* and *Chlamydia trachomatis* spiked into individual clinical samples could be stabilized by a mixed bed ion exchange resin (AMBERLITE™) for four days at room temperature.

Materials
Sample Processing Reagents:
Negative urine samples
Sample buffer
AMBERLITE™ MB-150 (Sigma)
*Neisseria gonorrhoeae* preparation
*Chlamydia trachomatis* preparation
Amplification Reagents:
*Neisseria gonorrhoeae* ODs as in Example 3
*Neisseria gonorrhoeae* ENDs as in Example 3
*Chlamydia trachomatis* Ods as in Example 2
*Chlamydia trachomatis* ENDs as in Example 2
Procedure Thirty urine samples were spiked with 800 *Neisseria gonorrhoeae*/ml and 800 *Chlamydia trachomatis*/ml. Additionally, seven ml of urine from each sample was transferred to a 15 ml conical tube containing 0.47 gms of AMBERLITE™ MB-150. Seven ml of urine from each sample was transferred to a 15 ml conical tube containing 1.4 gms of AMBERLITE™ MB-150. The tubes were immediately vortexed. The solutions containing 0.47 gms of AMBERLITE™ MB-150 were transferred to separate centrifuge tubes at four ml/tube. The tubes were placed in a centrifuge for 30 minutes at 2,000 g. The supernatant was decanted from the tubes and two ml of sample diluent was added to each tube. The tubes were placed in a 110° C. heat block for 30 minutes. The tubes were stored at −20° C. for four days.

The solutions containing 1.4 gms of AMBERLITE™ MB-150 were stored at room temperature for four days. The solution was transferred to separate centrifuge tubes at four ml/tube. The tubes were placed in a centrifuge for 30 minutes at 2,000 g. The supernatant was decanted from the tubes and two ml of sample diluent was added to each tube. The tubes were placed in a 110° C. heat block for 30 minutes.

The samples were amplified and results detected using the same procedure as in Example 2.

Results

The results are shown in the table below.

|  | 30 ml/1 hr, RT | | 10 ml/4 Days, RT | |
|---|---|---|---|---|
| Sample | GC Mean | CT Mean | GC Mean | CT Mean |
| M1 | 23268 | 21537 | 21653 | 20931 |
| M2 | 20225 | 21000 | 19875 | 21541 |
| M3 | 20272 | 27771 | 10136 | 26264 |
| M4 | 12857 | 14305 | 8846 | 25341 |
| M5 | 25794 | 26013 | 11086 | 34331 |
| M6 | 14770 | 30920 | 16201 | 33743 |
| M7 | 18639 | 34963 | 22402 | 34271 |
| M8 | 15790 | 24579 | 17808 | 38254 |
| M9 | 14108 | 32677 | 17859 | 37905 |
| M10 | 17934 | 30252 | 19888 | 33420 |
| M11 | 13759 | 31573 | 7405 | 28978 |
| M12 | 14593 | 28570 | 12464 | 33524 |
| M13 | 12734 | 30523 | 3564 | 32920 |
| M14 | 7877 | 21105 | 3276 | 24797 |
| M15 | 19072 | 32762 | 3416 | 22421 |
| F1 | 19098 | 17203 | 23589 | 33973 |
| F2 | 19239 | 22295 | 12790 | 22651 |
| F3 | 21398 | 23807 | 25668 | 35166 |
| F4 | 24030 | 16982 | 22403 | 35689 |
| F5 | 24875 | 31753 | 28853 | 34765 |
| F6 | 8470 | 26019 | 20349 | 36289 |
| F7 | 22544 | 27332 | 30676 | 36189 |
| F8 | 19781 | 12821 | 38465 | 40016 |
| F9 | 15061 | 32559 | 11625 | 36957 |
| F10 | 31090 | 34744 | 25470 | 43375 |
| F11 | 18029 | 38685 | 22737 | 36648 |
| F12 | 10285 | 35995 | 16472 | 39225 |
| F13 | 14550 | 30752 | 11455 | 37126 |
| F14 | 22820 | 32537 | 8562 | 36274 |
| F15 | 17515 | 38294 | 21233 | 36059 |
| MEAN | 18016 | 27678 | 17208 | 32968 |

Conclusions

Exposure to a mixed bed ion exchange resin (AMBERLITE™ MB-150) maintains the integrity of target organisms in individual clinical urine samples, throughout four days at room temperature.

EXAMPLE 7

Comparison of Ion Exchange Resin in Permeable Vehicle to Control Free Ion Exchange Resin The purpose of this Example was to determine if ion exchange resin, either in free contact to the sample or in a permeable vehicle, would have equivalent functional performance in the reduction of osmolality from a sample and in the amplification of extracted nucleic acid from said sample.

Materials
Sample Processing Reagents:
Spectra/Mesh® Polypropylene Filters 75uM
American International Electric Heat Sealer
Presision Systems Inc. Osmette A osmolality reader
AMBERLITE™ MB-150 (Sigma)
VWR 4oz. Specimen Collection Containers
15 ml Falcon™ Conical tubes
CT/GC Sample Diluent
10 Negative Urine Pools, each consisting of unique clinical samples.
Amplification and Assay Reagents:
*Chlamydia trachomatis* ODs as in Example 2
*Chlamydia trachomatis* ENDs as in Example 2
*Neisseria gonorrhoeae* ODs as in Example 3
*Neisseria gonorrhoeae* ENDs as in Example 3
Procedure AMBERLITE™ MB-150 ion exchange resin was first prepared by performing two washes in distilled water and vacuum drying the resin. The resin was then spread on a flat surface and allowed to dry overnight in a 37° C. incubator. A 2.4 g aliquot of the dried resin was then placed in an octagonal shaped heat sealed polypropylene mesh pouch. Ten of these pouches were constructed in such a manner that would maximize the exposure of the ion exchange resin to the sample. Modifications included reduction in size to accomplish the flat placement of said pouch at the bottom of a specimen collection container. Also, swelling of resin by sample absorption was accounted for. Each pouch was placed in each of 10 specimen collection containers. A 0.84 g aliquot of the dried resin was placed in each of 20 Falcon 15 ml conical tubes.

Ten 35 ml urine pools were made. Each urine pool was then spiked with 800 GC particles per ml and 800 CT EBs per ml. Baseline osmolality readings of untreated urine pools were taken. 20 mls of each urine pool was then placed in a specimen collection container with the ion exchange resin in a permeable vehicle. 14 mls each of the remaining urine pools was then divided to two Falcon 15 ml conical tubes containing free ion exchange resin. One tube was vortexed upon addition of the 7 ml urine pool. The other tube was not.

After 2 hours of treatment with the ion exchange resin, osmolality readings were taken on the treated urine pools. 4 mls of each treated urine was then subjected to 2000×g for 30 minutes. The supernatant was decanted and CT/GC sample diluent was then added to each each pellet at 2 ml per tube. The pellets were then vortexed for 5 seconds to resuspend the pellet. After heating the tubes in a heat block at 110° C. for 30 minutes, all samples were amplified and the results detected using the same procedure as in Example 2.

Results

The results are presented in the tables below as osmolality readings and *Chlamydia trachomatis* and *Neisseria gonorrhoeae* areas.

| Urine Pools | Untreated mOsm/kg | 2 hr. Incub of Amberlite in Urine Preservative Pouch (mOsm/kg) | Free AMBERLITE ™ Vortexed Post 2 hr. Incub. (mOsm/kg) | Free AMBERLITE ™ Vortexed Pre & Post 2 hr. Incub. (mOsm/kg) |
|---|---|---|---|---|
| Prov. M Pool 1 | 897 | 606 | 527 | 520 |
| Prov. M Pool 2 | 753 | 467 | 396 | 431 |
| Prov. M Pool 3 | 636 | 394 | 336 | 306 |
| Prov. F Pool 1 | 837 | 597 | 550 | 555 |
| Prov. F Pool 2 | 566 | 345 | 297 | 296 |
| LSU F Pool 1 | 738 | 448 | 401 | 412 |
| LSU F Pool 2 | 864 | 582 | 570 | 532 |
| LSU F Pool 3 | 852 | 636 | 568 | 523 |
| LSU M Pool 1 | 753 | 566 | 520 | frozen |
| LSU M Pool 2 | 850 | 602 | 539 | 511 |

| Urine Pools w/800 EBs per ml | 2 hr. Incub. of AMBERLITE ™ in Urine Preservative Pouch Mean CT Area (N = 3) | Free AMBERLITE ™ Vortexed Post 2 hr. Incub. Mean CT Area (N = 3) | Free AMBERLITE ™ Vortexed Pre & Post 2 hr. Incub. Mean CT Area (N = 3) |
|---|---|---|---|
| Prov. Male Pool 1 | 28942 | 35687 | 33368 |
| Prov. Male Pool 2 | 30376 | 28962 | 32419 |
| Prov. Male Pool 3 | 27650 | 25458 | 32562 |
| Prov. Female Pool 1 | 23353 | 22503 | 37514 |
| Prov. Female Pool 2 | 40927 | 20719 | 44077 |
| LSU Female Pool 1 | 31721 | 36125 | 25222 |
| LSU Female Pool 2 | 34144 | 25619 | 21939 |
| LSU Female Pool 3 | 27763 | 29901 | 35388 |
| LSU Male Pool 1 | 21111 | 26285 | 36393 |
| LSU Male Pool 2 | 33674 | 30290 | 32350 |
| Negative Control | 548 | 538 | 756 |
| Positive Control | 30021 | 29053 | 24737 |

| Urine Pools w/800 GC per ml | 2 hr. Incub. of AMBERLITE ™ in Urine Preservative Pouch Mean CT Area (N = 3) | Free AMBERLITE ™ Vortexed Post 2 hr. Incub. Mean CT Area (N = 3) | Free AMBERLITE ™ Vortexed Pre & Post 2 hr. Incub. Mean CT Area (N = 3) |
|---|---|---|---|
| Prov. Male Pool 1 | 20301 | 15005 | 20765 |
| Prov. Male Pool 2 | 30946 | 28747 | 28923 |
| Prov. Male Pool 3 | 23258 | 32763 | 24515 |
| Prov. Female Pool 1 | 18698 | 17048 | 15900 |

| | -continued | | |
|---|---|---|---|
| Prov. Female Pool 2 | 23825 | 15854 | 20507 |
| LSU Female Pool 1 | 16159 | 20085 | 9353 |
| LSU Female Pool 2 | 14090 | 19691 | 11598 |
| LSU Female Pool 3 | 13845 | 21970 | 22436 |
| LSU Male Pool 1 | 8389 | 19962 | 14579 |
| LSU Male Pool 2 | 19499 | 21274 | 10361 |
| Negative Control | 400 | 1086 | 464 |
| Positive Control | 24487 | 9544 | 32709 |

Conclusions

Ion exchange resin, either in free contact to the sample or in a permeable vehicle, has equivalent functional performance in terms of osmolality reduction and amplification.

A significant difference is observed in osmolality between the untreated pools and the same pools treated with the pouched resin (p value=4.42E-05). However, no significant difference is observed between the pouched resin and either the free resin with a pre-incubation vortex step (p value=0.06, assuming unequal variance due to frozen sample) or free resin without a pre-incubation vortex step (p value=0.25). Additionally, if the frozen sample is eliminated in the comparison between the pouched resin and the free resin with a pre-incubation vortex step (p value=0.19, assuming equal variance), then the difference is even less significant. The minimum requirement for functional removal of salts from the sample is simply physical contact.

No significant difference is observed in *Chlamydia trachomatis* area units for the pouched resin vs. either the free resin with a pre-incubation vortex step (p value=0.25) or free resin without a pre-incubation vortex step (p value=0.46). The same observation can be found for *Neisseria gonorrhoeae* area units. For the pouched resin vs. either the free resin with a pre-incubation vortex step (p value=0.73) or free resin without a pre-incubation vortex step (p value=0.39), no statistical difference could be found.

EXAMPLE 8

The Stabilization of a Sample by Ion Exchange Resin in a Permeable Vehicle for Testing by a Molecular Diagnostic Process The purpose of this Example was to determine if ion exchange resin in a permeable vehicle would provide for the stabilization of target organisms for subsequent testing by Strand Displacement Amplification (SDA) of nucleic acid of such organisms.

Materials

Sample Processing Reagents:

Same as for Example 7.

Amplification and Assay Reagents:

Same as for Example 7.

Procedure

Same as for Example 7 except, after 5 and 7 days of treatment with the ion exchange resin, osmolality readings were taken on the urine pools treated with free ion exchange resin and urine pools treated with the ion exchange resin in a permeable vehicle. Urine pools were subjected to room temperature storage for the duration of the 5 and 7 day time periods before analysis.

Urine pools that were treated with the ion exchange resin in a permeable vehicle were also subjected to testing by strand displacement amplification after 5 and 7 days. At each timepoint, a 4 ml volume of each treated urine pool was subjected to 2000×g for 30 minutes. The supernatant was decanted and CT/GC sample diluent was then added to each pellet at 2 ml per tube. The pellets were then vortexed for 5 seconds to resuspend the pellet. After heating the tubes in a heat block at 110° C. for 30 minutes, all samples were amplified and the results detected using the same procedure as in Example 2.

Results

The results are presented in the tables below as osmolality readings and *Chlamydia trachomatis* and *Neisseria gonorrhoeae* areas.

| Urine Pools | 2 hr. Incub of AMBERLITE ™ in Urine Preservative Pouch (mOsm/kg) | 5 day Incub of AMBERLITE ™ in Urine Preservative Pouch (mOsm/kg) | 7 day Incub of AMBERLITE ™ in Urine Preservative Pouch (mOsm/kg) |
|---|---|---|---|
| Prov. M Pool 1 | 606 | 539 | 539 |
| Prov. M Pool 2 | 467 | 402 | 405 |
| Prov. M Pool 3 | 394 | 265 | 261 |
| Prov. F Pool 1 | 597 | 577 | 565 |
| Prov. F Pool 2 | 345 | 274 | 272 |
| LSU F Pool 1 | 448 | 427 | 430 |
| LSU F Pool 2 | 582 | 554 | 584 |
| LSU F Pool 3 | 636 | 537 | 533 |
| LSU M Pool 1 | 566 | 501 | 498 |
| LSU M Pool 2 | 602 | 481 | 483 |

-continued

| Urine Pools w/800 EBs per ml | 2 hr. Incub. of AMBERLITE ™ in Urine Preservative Pouch Mean CT Area (N = 3) | 5 day Incub. of AMBERLITE ™ in Urine Preservative Pouch Mean CT Area (N = 3) | 7 day Incub. of AMBERLITE ™ in Urine Preservative Pouch Mean CT Area (N = 3) |
|---|---|---|---|
| Prov. Male Pool 1 | 27542 | 26838 | 34194 |
| Prov. Male Pool 2 | 35377 | 37790 | 37918 |
| Prov. Male Pool 3 | 26533 | 44240 | 36227 |
| Prov. Female Pool 1 | 30848 | 36650 | 17570 |
| Prov. Female Pool 2 | 30682 | 34849 | 34969 |
| LSU Female Pool 1 | 32517 | 18689 | 30677 |
| LSU Female Pool 2 | 23494 | 32481 | 26919 |
| LSU Female Pool 3 | 29470 | 39160 | 27402 |
| LSU Male Pool 1 | 24556 | 31976 | 31595 |
| LSU Male Pool 2 | 27891 | 32687 | 37414 |
| Negative Control | 515 | 520 | 573 |
| Positive Control | 18894 | 19081 | 895 |

| Urine Pools w/800 GC per ml | 2 hr. Incub. of AMBERLITE ™ in Urine Preservative Pouch Mean GC Area (N = 3) | 5 day Incub. of AMBERLITE ™ in Urine Preservative Pouch Mean GC Area (N = 3) | 7 day Incub. of AMBERLITE ™ in Urine Preservative Pouch Mean GC Area (N = 3) |
|---|---|---|---|
| Prov. Male Pool 1 | 19020 | 10052 | 10043 |
| Prov. Male Pool 2 | 25770 | 32026 | 32255 |
| Prov. Male Pool 3 | 26110 | 21493 | 34625 |
| Prov. Female Pool 1 | 22379 | 5929 | 7031 |
| Prov. Female Pool 2 | 20497 | 15707 | 11580 |
| LSU Female Pool 1 | 18213 | 9314 | 5382 |
| LSU Female Pool 2 | 18517 | 16579 | 11179 |
| LSU Female Pool 3 | 26272 | 17937 | 10682 |
| LSU Male Pool 1 | 7613 | 21325 | 9332 |
| LSU Male Pool 2 | 11777 | 21289 | 15567 |
| Negative Control | 834 | 518 | 775 |
| Positive Control | 21034 | 25312 | 15476 |

Conclusions

Osmolality readings taken after 2 hours, 5 and 7 days of treatment with free ion exchange resin and ion exchange resin in a permeable vehicle shows the continuation of the marked decrease in osmolality from untreated urine. No statistical difference was seen within this time frame (2 hr vs. 5 day: p value=0.17; 2 hr vs. 7 day: p value=0.18). This establishes that ion exchange resin effects the sample throughout a time period where stabilization of target nucleic acid would take place.

A comparison of the amplification and detection of extracted *Chlamydia trachomatis* and *Neisseria gonorrhoeae* nucleic acid from all urine pools treated with ion exchange resin in a permeable vehicle for 2 hours, 5 and 7 days, shows no statistically significant drop in signal with time. It was shown in Example 4 that *Neisseria gonorrhoeae* is unstable in urine samples stored at room temperature for greater than 24 hours. It is shown here that ion exchange resin in a permeable vehicle provides for the stabilization of organisms for up to 7 days allowing subsequent testing by strand displacement amplification of organism nucleic acid.

While the invention has been described with some specificity, modifications apparent to those with ordinary skill in the art may be made without departing from the scope of the invention. Various features of the invention are set forth in the following claims.

What is claimed is:

1. A method for stabilizing a sample containing cells prior to cell lysis, said method comprising combining the sample with a mixed bed ion exchange resin wherein said combining results in stabilization of said sample sufficient for room temperature transport prior to cell lysis.

2. The method of claim 1 wherein the sample is combined with the ion exchange resin for at least 15 minutes.

3. The method of claim 1 further comprising separating the ion exchange resin from the sample.

4. The method of claim 3 wherein separation of ion exchange resin from sample comprises physical removal of the ion exchange resin from the sample.

* * * * *